United States Patent [19]

Zweig

[11] Patent Number: 5,418,143

[45] Date of Patent: May 23, 1995

[54] TEST ARTICLE AND METHOD FOR PERFORMING BLOOD COAGULATION ASSAYS

[75] Inventor: Stephen E. Zweig, Los Gatos, Calif.

[73] Assignee: Avocet Medical, Incorporated, Los Gatos, Calif.

[21] Appl. No.: 196,816

[22] Filed: Feb. 9, 1994

Related U.S. Application Data

[63] Continuation of Ser. No. 874,667, Apr. 27, 1992, abandoned.

[51] Int. Cl.[6] ............ C12Q 1/56; C12N 11/08; G01N 33/86
[52] U.S. Cl. ................... 435/13; 435/180; 436/69; 422/60; 530/381
[58] Field of Search .......... 435/13, 176, 180, 182; 422/56, 57, 60; 436/69; 530/381, 384

[56] References Cited

U.S. PATENT DOCUMENTS

| | | | |
|---|---|---|---|
| 3,884,896 | 5/1975 | Blomback | 260/112.5 |
| 4,273,873 | 6/1981 | Sugitachi | 435/180 |
| 4,458,015 | 7/1984 | Jering et al. | 435/23 |
| 4,640,893 | 2/1987 | Mangel | 435/23 |
| 4,755,461 | 7/1988 | Lawson et al. | 435/13 |
| 4,756,884 | 7/1988 | Hillman et al. | 422/73 |
| 4,774,192 | 9/1988 | Terminiello | 436/530 |
| 4,861,712 | 8/1989 | Bartl et al. | 435/13 |
| 4,910,150 | 3/1990 | Doeding et al. | 436/69 |
| 4,935,346 | 6/1990 | Phillips et al. | 435/14 |
| 5,059,525 | 10/1991 | Bartz | 435/13 |

OTHER PUBLICATIONS

Nemerson, "Tissue Factor and Hemostasis", *The Journal of the American Society of Hematology*, 71:1–8, (1987).

Janson et al., "Species Specificity of Tissue Thromboplastin", *Research Institute for Internal Medicine, University of Oslo, and the Animal Department, Rikshospitalet*, 14:440–444 (1984).

*Primary Examiner*—William H. Beisner
*Assistant Examiner*—Ralph Gitomer
*Attorney, Agent, or Firm*—Townsend and Townsend Khourie and Crew

[57] ABSTRACT

A test article for determining coagulation capability in a blood sample comprises a porous membrane having a coagulation initiator and substrate impregnated therein. The pore dimensions and composition of the membrane are selected so that only blood plasma can pass into the interior of the membrane, where coagulation is initiated. The substrate is activated by a component of the coagulation pathway, typically thrombin, and produces a detectable signal upon activation. By utilizing membrane matrix materials which are substantially free from interference with the coagulation pathway, accurate results can be achieved.

27 Claims, 2 Drawing Sheets

TEST ARTICLE AND METHOD FOR PERFORMING BLOOD COAGULATION ASSAYS

This is a continuation of application Ser. No. 07/874,667, filed Apr. 27, 1992, now abandoned.

BACKGROUND OF THE INVENTION

1. Field of the Invention

The present invention-relates generally to blood coagulation testing, and more particularly to a test article comprising the reagents necessary for such an assay and methods which rely on the generation of a fluorescent or other visible signal from the test article.

Blood coagulation tests may be performed for a variety of purposes, including determination of bleeding susceptibility of patients undergoing surgery and monitoring of patients undergoing anti-coagulation therapy for the prevention of blood clots. A variety of coagulation tests are presently in use. One of the most popular is the "prothrombin time" (PT) test which relies on induction of the extrinsic coagulation pathway, and another is the "activated partial thromboplastin time" (APTT) test which relies on induction of the intrinsic coagulation pathway. Both the extrinsic and intrinsic coagulation pathways result in the production of thrombin, which is a proteolytic enzyme which catalyzes the conversion of fibrinogen to fibrin. Such conversion is an essential function in the clotting mechanism. Conveniently, thrombin production can be monitored by exposure of a patient blood sample to a synthetic thrombin substrate peptide, cleavably bound to a reporter molecule which is activated by thrombin cleavage. The reporter molecule produces an observable change, such as color production or fluorescence; and thrombin activity (which is a measure of the blood's coagulation capability) is assessed by optical means.

Heretofore, such blood coagulation tests have tended to be complex, with performance generally limited to clinical laboratories. While such centralized testing may be adequate for surgical patients, visiting a doctor's office or a clinic on a regular basis to monitor anti-coagulation therapy is less acceptable. Thus, the need for a convenient and practical home coagulation monitoring test is apparent.

The technical challenges in devising a coagulation test which is simple enough to be administered by the patients themselves, however, are substantial. The test must be extremely simple, low cost, robust, and must permit use with widely varying volumes of whole blood. Blood sampling in a home environment is generally limited to the "fingerstick" method (where a finger is pricked by a small needle mounted on a spring-loaded device), which produces relatively uncontrolled volumes of whole blood, generally being from 5 to 30 $\mu$l. Additionally, it would be desirable if the blood coagulation test could be performed at room temperatures, eliminating the need for elaborate temperature control apparatus.

Successful home blood tests have been devised for other chemistries, such as cholesterol and glucose. Among the most suitable devices for home use are "test strips" comprising a layer of absorbent material having appropriate impregnated regions to perform a desired analysis. For example, a test strip for performing blood glucose analysis, available from Lifescan, Inc., Milpitas, Calif., relies on applying a drop of blood to a polyamide membrane having impregnated reagents which produce a chromogenic reaction in response to the glucose level in the applied blood. No equivalent test devices have been developed for measuring blood coagulation capability. While certain test articles for measuring coagulation have been proposed, even the most simple employ multiple-layers, where premeasured volumes of blood must be applied. These tests are generally performed in a clinical setting.

The nature of the blood coagulation pathways renders the performance of single layer test strip coagulation assays problematic. Blood coagulation involves a series of complex and poorly understood enzymatic reactions that are highly sensitive to surface interface effects. Additionally, blood contact with certain materials can inactivate the enzymes necessary for induction of the coagulation pathways. Thus, most previous coagulation assays have utilized containers with minimal surface area to reduce the likelihood of inadvertent activation or inhibition of the coagulation pathway. Test strip assays, in contrast, are generally performed in highly porous materials having a very large surface area. Thus, such test strip membranes would generally be contraindicated for use in blood coagulation assays.

For the above reasons, it would be desirable to provide simplified test articles and methods for measuring a patient's coagulation capability. The test articles and methods should be sufficiently simple and reliable to permit tests to be performed by untrained individuals, particularly by the patients themselves in a home setting. Preferably the tests should require only a single step, such as the application of a drop of blood onto a test article, followed by automated reading of the test results. The test should not be sensitive to variations in blood sample volume and should be capable of performance with minimal or no temperature control. In particular, it would be desirable to provide test articles and methods employing a porous membrane test strip, where the test strip has substantially no effect on the blood coagulation pathway being measured.

2. Description of the Background Art

Thrombin substrates suitable for use in coagulation assays are described in U.S. Pat. Nos. 3,884,896 and 4,640,893. A tableted form of thromboplastin having improved stability resulting from calcium separation is described in U.S. Pat. No. 4,755,461. A dry reagent consisting of thromboplastin and a thrombin substrate useful for liquid phase coagulation assays is described in U.S. Pat. No. 4,458,015.

An assay system for measuring glucose in blood, consisting of an inert porous matrix impregnated with reagents which produce a light-absorbing reaction, is described in U.S. Pat. No. 4,935,346. A blood sample is applied to one side of the matrix and reflectance measured on the opposite side. The membrane used in this system tends to rupture (lyse) red cells. This causes high levels of hemoglobin to permeate the interior of the membrane; and high levels of hemoglobin can be observed on the opposite side of the matrix. The '346 patent teaches that for analytes such as glucose, this effect may be overcome by using a particular chemistry that produces an optical signal with spectral properties that can be distinguished over the dominating spectra of this released hemoglobin, and reading the results with dual wavelength optics that correct for the hemoglobin spectra. Such an approach would not work for the very delicate, and hemoglobin sensitive, thrombin substrate coagulation chemistry. Another assay system suitable for measuring blood glucose, cholesterol, and urea is described in U.S. Pat. No. 4,774,192. The necessary reagents are impregnated in a structure, such as a porous membrane or bibulous film, which may be an asymmetric membrane. The '192 patent also suggests the use of flow control agents for controlling sample distribution in the structure.

U.S. Pat. Nos. 4,861,712, 4,910,510, and 5,059,525, describe multi-layer test articles suitable for monitoring blood coagulation. The '712 patent describes a complex structure consisting of a filamentous material, and a water soluble non-ionic polymer which coats and impregnates the filamentous material. This structure may contain thromboplastin and a detectable thrombin substrate, and is useful for monitoring a number of blood coagulation parameters, including prothrombin time.

The '525 patent describes a complex dry reagent for blood coagulation tests that contains a carrier material, and dried in it: a protease reactive to prothrombin (or Factors VII–X), a chromogenic protease substrate, a buffer, and a second coagulation factor. The inclusion of a protease into the dry reagent is useful for performing assays for coagulation factors, such as factor X, that must first be activated by proteolytic cleavage before their enzymatic activity can be measured.

U.S. Pat. No. 4,756,884, describes a capillary flow device for measuring blood characteristics, including prothrombin time.

SUMMARY OF THE INVENTION

According to the present invention, test articles and methods are provided for performing blood coagulation assays using simplified protocols and formats. The test articles comprise a permeable membrane impregnated with a coagulation initiator capable of initiating either an extrinsic or intrinsic coagulation pathway, and a substrate which produces a detectable signal upon activation by a preselected component of the coagulation pathway which has been initiated. The membrane is selected to be non-lytic of blood cells, and capable of excluding these intact red cells from at least the portion of the membrane interior immediately underneath the optical viewing surface side of the membrane that is opposite to the sample application side. Additionally, the membrane must be substantially free from interference with initiation and continuation of the coagulation pathway, particularly being free from surface interaction(s) with enzymes and other components of the pathway which can lead to inactivation or false activation of the pathway. Such membranes may be composed of materials which are themselves free from such surface (interactions), or may be composed of other materials which are coated or blocked with proteins or other substances which reduce the undesirable surface interaction(s). A preferred membrane is composed of polysulfone, particularly being an asymmetric polysulfone membrane.

According to the method of the present invention, a blood volume is applied to one face of the permeable membrane where it is absorbed into the interior of the membrane in the presence of the coagulation initiator and substrate. Blood coagulation is thus initiated, and production of the preselected component of the coagulation pathway causes activation of the substrate to produce the detectable signal, usually on the opposite face of the membrane. The pore dimensions of the membrane are selected so that the red blood cells (erythrocytes) of the sample are maintained on or near the application face, and do not enter into that portion of the interior that is directly beneath the observation face of the membrane where they could interfere with generation of the detectable signal. Moreover, the absorption volume of the membrane is selected so that it will receive a relatively low volume of the separated blood plasma, with the excess whole blood remaining on the application surface. In this way, the test article can accomodate even very low test volumes, and actual amount of blood sample applied to the test article is not critical.

The results of the test will typically be read by an automated detector or test system, typically comprising a fluorometer in the case of a fluorescent detectable signal. The automated detector will usually include control circuitry comprising a timer to permit detection at an appropriate time or over an appropriate time period of the test, and means for calculating the coagulation "value." Usually, the control circuitry will include a temperature control means for maintaining the sample at a predetermined temperature. Alternatively, the automated detector can be temperature compensated to adjust the initially determined coagulation "value" upward or downward to compensate for variations in the sample temperature.

DESCRIPTION OF SPECIFIC EMBODIMENTS

The test articles of the present invention comprise a porous membrane in a form suitable for applying blood, typically in small volumes in the range from 3 $\mu l$ to 50 $\mu l$, usually from 5 $\mu l$ to 30 $\mu l$, and for detecting a visible signal on the membrane surface, typically on an opposite side of the membrane. The membrane can be formed as a sheet, strip, disk, tape (reel), or the like, and a single membrane can be used for one or more tests. When used for multiple tests, the blood samples will typically be spotted onto different locations, either simultaneously or sequentially. The membrane will typically be very thin, usually having a thickness from 0.1 mm to 0.3 mm, in order to limit the volume of blood plasma needed to reach saturation. Excess blood will be maintained on the membrane surface to which it has been applied, with only a desired volume of plasma, typically in the range from 0.5 $\mu l$ to 2 $\mu l$, entering the membrane interior. After the membrane or a selected portion thereof becomes saturated, the blood proteins and test reagents will diffuse relatively slowly permitting the test protocol to be performed, as described in detail hereinafter.

Figure 1:
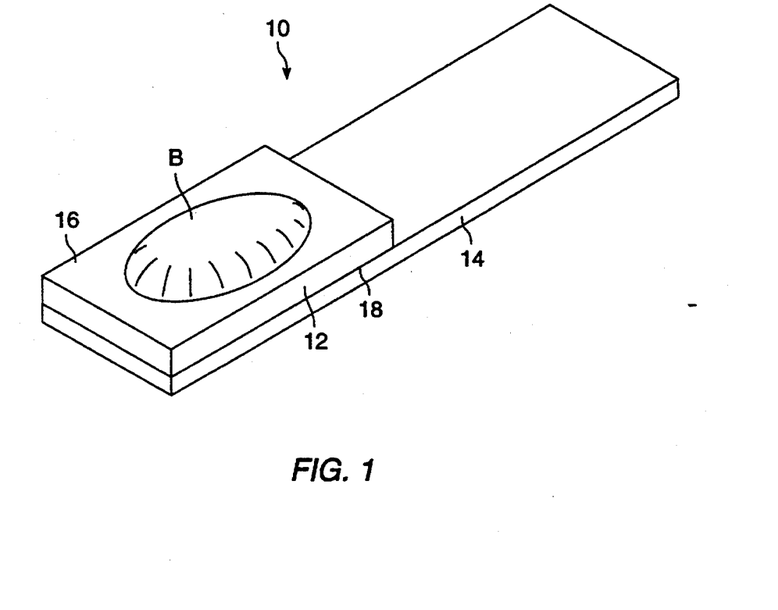
FIG. 1 is a perspective view of an exemplary embodiment of a test article constructed in accordance with the principles of the present invention.

An exemplary test article 10 constructed in accordance with the principles of the present invention is illustrated in FIG. 1. The test article 10 includes a porous membrane structure 12 mounted on a support structure 14, typically a handle to permit manipulation of the test article by the user. The test article 10 is used by applying an unmeasured drop of blood to an applicator face 16 of the porous membrane 12. At least a portion of the blood plasma is absorbed into the membrane 12 and, as a result of coagulation initiated within the 12 as described hereinafter, a detectable signal is produced on an indicator face 18 of the membrane, where the indicator face is typically laterally opposed to the applicator face 16. The detectable signal produced on the indicator face 18 will be visible through the handle 14, with the handle being transparent, having a suitable viewing aperture (not shown), or the like. Observance of the detectable signal permits continuous assessment of the coagulation reaction and determination of the coagulation capability of the blood sample.

The porous membrane structure 12 will be composed of a hydrophilic (bibulous), non-swellable polymeric matrix material having pore dimensions which permit entry of blood plasma and proteins while excluding blood cells, particularly red blood cells (erythrocytes). The membrane should be composed of a single, continuous polymeric material with a foam-like structure consisting of a torturous network of channels having widths on the order of microns ($\mu$m). The torturous network of channels is "densely packed" in that the "void volume" occupied by the empty space of the channels is an appreciable percentage of the total membrane volume, typically 10% or greater. Since all reaction chemistry, and subsequent signal generation, takes place in the void volume, a high void volume is desirable for producing a strong signal. A torturous network of channels is desired over straight and direct pores, (such as the short, direct pores obtained with nucleopore membranes), as longer average channel lengths tend to produce an increasing isolation between the zone of the membrane where reaction chemistry is occurring, and the excess sample remaining on the surface of the membrane. This helps to render the system less sensitive to variations in applied sample volume.

As discussed in detail hereinafter, the porous membrane structure 12 will be impregnated with reagents necessary to induce coagulation in blood plasma which enters the interior of the porous matrix and to produce a detectable signal as an indication of the coagulation capability of the blood. It is particularly critical to the present invention that the polymeric matrix material of the porous membrane 12 be substantially free from interference with the coagulation pathway which is being induced. In particular, the polymeric matrix material should be free from surface effects, interactions, and artifacts which might induce coagulation or inactivate components such as enzymes, of the initiated pathway. Unintended initiation of a coagulation pathway could lead to false positive determinations while enzyme inactivation could lead to false negative determinations. It is therefore important that the polymeric matrix material have no promoting or diminishing effect on the coagulation reactions occurring within the membrane.

The following criteria can be used to determine if a membrane is acceptable for use in the test articles and methods of this invention:

A: The membrane must have a pore geometry and size distribution that excludes red cells from penetrating through to the opposite face of the membrane.

B: The membrane must be hydrophilic (or be treated to be hydrophilic) so that plasma from a blood sample can completely permeate the membrane within a few seconds, preferably within 1–2 seconds.

C: The membrane must be either blood cell compatible (or be treated to become blood cell compatible) so that whole blood applied to the membrane will not lyse. Further, the membrane must have sufficient ability to separate blood cells from plasma so that only red cell-free and hemoglobin-free plasma penetrates through to the side of the membrane opposite to the sample application side. This ability to generate red cell-free and hemoglobin-free plasma must persist over a useful range of hematocrits, over at least a 30 to 55% hematocrit range.

D: The membrane must be sufficiently coagulation neutral (or be treated to become coagulation neutral) as to permit an extrinsic (or intrinsic) coagulation pathway to proceed. This can be determined experimentally by permeating the membrane with a reaction mixture (described in the Experimental section), drying, and then reactivating with a sample of whole blood or plasma. Many membranes (Dominic-Hunter Asypor, Pall corporation Biodyne "C", etc.) totally quench the extrinsic (or intrinsic) coagulation pathways. The membrane must be sufficiently coagulation neutral as to permit both normal plasma, and extrinsic pathway (or intrinsic pathway) factor deficient plasma, to successfully react and produce clinically accurate results.

E: The membrane must provide volume tolerance (or be treated to provide volume tolerance) such that it produces substantially similar results when treated with varying volumes of whole blood ranging roughly in amount from about 5 to 30 microliters.

F: The membrane's optical properties must be compatible with the observation wavelengths used in the assay. For example, the membrane's intrinsic fluorescence must not dominate the fluorescence of the thrombin substrate used in the reaction.

G: The membrane must be sufficiently dimensionally stable when wet and dry so as to withstand normal processing during manufacturing, and to avoid distorting test results during the course of the reaction.

As will be discussed in more detail in the Experimental section, very few membrane types meet all these criteria. As an example, polyamide membranes, such as the Pall Corporation Biodyne "A" "B" and "C" series, fail test C. Negatively charged polyamide membranes, such as Biodyne "C" fail both tests C and D. Cellulose based asymmetric pore membranes, such as the Asypor series produced by Dominic Hunter, fail test D. Glass fiber filter materials, such as Schlechter & Schuell 34G, fail test E. One untreated membrane type which has been found to meet all these criteria is an asymmetric polysulfone membrane, such as BTS-25 0.45 $\mu$m Asymmetric polysulfone membrane available from Filterite/Memtec. Other suitable membranes, however, could be identified using the above criteria.

A variety of other membrane materials may also be used so long as the membranes are treated to meet certain of the criteria set forth above. For example, if use with plasma samples rather than whole blood samples is desired, polyamides may be blocked to enhance coagulation neutrality, as defined above. Typically, such blocking may be achieved by preincubating the membrane with a suitable protein solution prior to or simultaneous with introducing the remaining reagents.

The pore dimensions of the polymeric matrix will be selected to permit the absorption of the blood plasma and proteins from the applied blood sample, while excluding the cellular blood components, particularly the red blood cells which have been found to interfere with the coagulation detection chemistry. Pore dimensions of the matrix will generally be in the range from 0.05 μm to 5 μm, typically being in the range from 0.1 μm to 1.0 μm. In a preferred embodiment, the pore dimensions will be asymmetrically arranged, with larger pores disposed on the application face 16 of the membrane structure 12 and smaller pores being disposed on the indicator face 18. Such an asymmetric pore size distribution is beneficial since it permits larger pores to be present at the interface where the blood is applied, facilitating rapid penetration of the blood into the membrane. Smaller pores, however, on the opposite face of the membrane, separate red cells from plasma, and present a red cell and hemoglobin free plasma to the optical detection apparatus. Preferably, the pore dimensions on the applicator face 16 of the membrane structure 12 will be in the range from 2 μm to 50 μm, and on the indicator face 18 will be in the range from 0.1 μm to 1.0 μm.

The polymeric matrix material will be non-swellable. That is, the matrix will usually not substantially deform when exposed to an aqueous solution, such as blood plasma, thus retaining its original conformation and size. Typically, the change in volume of the porous membrane structure 12 will be less than 20%, preferably less than 10%, upon exposure to blood plasma or other aqueous media.

A particularly preferred polymeric matrix material meeting all of the above requirements is a 0.45 μm asymmetric polysulfone membrane material available from Filterite-Memtec. Memtec America, 9690 Deeveco Road, Ste. 7, Timonium, Md. 21093. the preferred material is catalog number BTS-25 media.

Chemical reagents necessary for performing the blood coagulation assays of the present invention are impregnated within the polymeric matrix material just described. Necessary reagents include a coagulation initiator which initiates a preselected event or stage in either an extrinsic or intrinsic coagulation pathway and a substrate which is activated by a component which is produced in a subsequent stage of the coagulation pathway. A buffer will also be provided to maintain the test pH within a range compatible with the coagulation pathway, and optional reagents include flow control agents which decrease chromatographic separation of blood proteins entering the membrane, cofactors which sustain or enhance the chemical reactions of the coagulation pathway, stability enhancers, and pigments which enhance the optical characteristics of the test article. Typically, these reagents will be combined in one or more aqueous solution(s) (which may further comprise the membrane blocking agent(s) described above) which are applied to all or a portion of the polymeric matrix material. The matrix material may then be dried or lyophilized (and optionally mounted on the handle 14) to form a test article having the reagents non-covalently adsorbed therein. In some cases, it may be possible to covalently attach at least some of the reagents, although covalent attachment will usually not be necessary.

The test article thus prepared may be used immediately or stored for subsequent use. The absorbed reagents will be reconstituted by applying the blood sample which causes blood plasma to enter the interior of the porous membrane matrix, and to wet the reagents.

A variety of suitable coagulation initiators may be employed. These initiators will trigger the coagulation pathways at the standard points that are commonly used for medical tests. For example, the extrinsic coagulation pathway initiator will combine with factor VII and calcium to activate factor X. The intrinsic coagulation pathway initiator will activate factor XII to in turn activate factor XI. Suitable initiators of the extrinsic coagulation pathway are well known in the art and include thromboplastin, and the like. Suitable initiators for the intrinsic coagulation pathway are also well known in the art and include ellagic acid, kaolin, silica, and the like. Description of these and other initiators are provided in *Laboratory Evaluation of Hemostasis and Thrombosis* (Third Edition), 1983, Marjorie S. Sirridge and Reaner Shannon, Lea & Febiger, Philadelphia; and *Hemostatis and Thrombosis, a conceptual approach* (Second Edition), 1983, Jack Hirsh and Elizabeth Brain, Churchill Livingstone, New York, the disclosures of which is incorporated herein by reference. The selected coagulation initiator will be applied to the matrix in an amount sufficient to initiate coagulation in the expected sample volume of blood plasma. For example, a suitable amount of thromboplastin will be sufficient to provide a concentration in the range from 100 mg/l to 10 g/l when reconstituted in the blood plasma.

Suitable substrates for monitoring the coagulation reaction include certain derivatized peptides which are activated by the thrombin that is produced as a final event in both the extrinsic and intrinsic coagulation pathways. The peptides are cleavably linked to a reporter molecule, such as a chromogenic, chemiluminescent, or fluorogenic molecule. Thrombin is able to recognize the peptide, cleave the cleavable linker, and cause a change in the optical characteristics of the reporter molecule resulting in a detectable signal, such as color change, light emission, or fluorescence. Numerous suitable thrombin substrate peptides are described in U.S. Pat. Nos. 3,884,896; 4,070,245; and 4,169,051, the disclosures of which are fully incorporated herein by reference. These substrate peptides are generally (but not always) of the form B—X—Y—Arg—NH—R, where B is a blocking group, X—Y is a dipeptide (often Val—Pro, Gly—Pro, Phe—Val, etc.), and R is a reporter molecule linked to the peptide by a hydrolyzable NH bond. Typically R will change its optical state after the NH linkage has been hydrolyzed by thrombin. An exemplary substrate peptide is N—t—Boc—Val—Pro—Arg linked to a 7-amido-4-methylcoumarin reporter molecule. This substrate is commercially available from the Sigma Chemical Company, St. Louis, Mo.

Particularly preferred is the use of fluorogenic reporter molecules, such as 7-amido-4-methylcoumarin, rhodamine 110, aminoquinolines, aminonapthalenes, benzofurazans, acridines, and the like. The polymeric matrix material of the porous membranes utilized in the present invention will typically be very thin, usually in the range from 0.1 to 0.3 mm as described above, which defines an insufficient optical path to provide a clear color signal when employing many chromogenic substrates. With chromogenic substrates, in order to increase the color evolved to a sufficient level for detection, it is often necessary to increase the concentration of the substrate within the membrane to unphysiological levels. Such high substrate concentrations, typically $10^{-4}$M and greater, are significantly higher than the concentration of the normal fibrinogen substrate for thrombin, and have a tendency to interfere with the coagulation pathways. Additionally, such high substrate levels take a substantial time for the thrombin enzyme to fully convert. These effects tend to degrade the clinical utility of the assay. These effects can be avoided, and superior results can be obtained, by using substrate concentrations below $10^{-4}$M. It has been found herein that by employing fluorescent reporter molecules, strong signals can be obtained with substrate concentrations below $10^{-4}$M, typically as low as $10^{-5}$M and below.

A buffer will be impregnated within the polymeric matrix material in order to provide a pH compatible with the coagulation pathway. Particularly suitable are Tris buffers with pH varying from about 7 to 8 depending on the matrix. A buffer which maintains the pH at about 7.5 is preferred for the preferred polysulfone asymmetric membrane material and extrinsic pathway.

Coagulation cofactors, such as calcium, may be utilized to sustain the coagulation pathway. In particular, it may be necessary to use calcium, such as in the form of calcium chloride, when testing blood samples that have previously been anti-coagulated with a calcium chelator. Should calcium be required, the stability characteristics of the reagent may be improved by isolating it apart from the thromboplastin within the membrane, either by being physically separated, or by being microencapsulated.

Fluid control agents may also be impregnated within the membrane in order to increase the viscosity of the blood plasma and limit chromatographic separation of the reaction components. Suitable flow control agents include high molecular weight polymers, such as hydroxypropylcellulose, polyvinyl alcohol, and the like. Additionally, the inclusion of pigments within the matrix can enhance the emission of fluorescent light. Suitable pigments include small, light-scattering particles of a material that does not interfere with the coagulation pathway. A suitable pigment has been found to be composed of styrene-acrylic copolymer particles, available from Rohm & Haas Company, Philadelphia, Penn., under the tradename Ropaque ™ OP-84.

Figure 2:
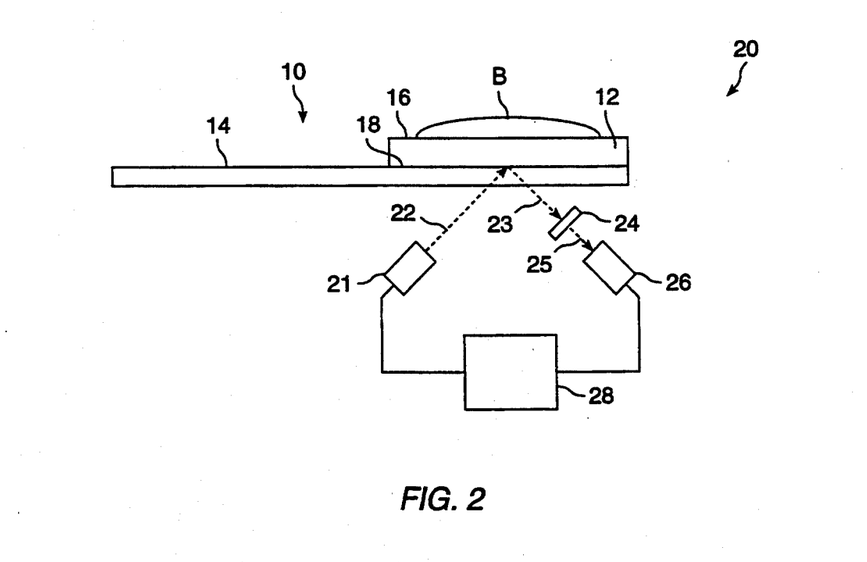
FIG. 2 is a block diagram of a test system useful for reading results from the test article when employed in a blood coagulation assay performed in accordance with the principles of the present invention.

Exemplary amounts of the various reagents which are impregnated within a portion of the polymeric matrix material intended for performing a single prothrombin time assay are as follows.

centered at the emission wavelength, with the light 25 passing through the filter being detected by detector 26. For the examples disclosed employing 4-amido-7-methylcoumarin as the reporter molecule, the excitation wavelength will typically be 365 nm while the detection wavelength will be 450 nm. Alternative fluorescent reporter molecules with longer excitation and emission wavelengths, however, are possible. In general, longer wavelengths are preferred because the cost of the light source is less, and the efficiency of detection can be improved. The test system 20 further includes control circuitry 28 which analyzes the amount of light detected by detector 26 over time according to a desired coagulation test protocol, such as the prothrombin test (PT), the activated partial thromboplastin test (APTT), and the like. Usually, the control circuitry 28 will include a timer, which may be initiated manually or as the result of a particular event, such as application of blood to the membrane 12. Optionally, the control circuitry will include a temperature measurement capability so that variations in temperature can be taken into account when interpreting the test results. Alternatively, the test system 20 could include a temperature controlled chamber in order to maintain the blood at a particular temperature, typically 37° C. If a temperature controlled chamber is used, it will be advantageous to mount the reagent membrane on a transparent substrate material, and to pre-equilibrate this substrate to the desired test temperature before applying the sample. This facilitates rapid equilibration of the applied sample to the desired temperature. Optionally, a covering layer may be placed on top of the sample to further facilitate rapid temperature stabilization. The control circuitry will further include calculating means, such as a microprocessor, for calculating the coagulation "value" of the blood. Many algorithms to compute a prothrombin time or other coagulation value are possible. The following is an example optimized for a four minute duration prothrombin time test designed to be operated at room temperature (23° C.), where reaction times are slower. Fluorescence data are collected at 10-second time points, i.e., F(0), F(10), F(20) . . . F(240). This array F(t), is then normalized to correct for differences in

| | Reagent Incorporation | | | |
|---|---|---|---|---|
| Reagent | Broad Range | | Narrow Range | |
| Thromboplastin | 0.1 g/L | to 12 g/L | 3 g/L | to 9 g/L |
| Substrate | $10^{-7}$ M/L | to $10^{-3}$ M/L | $10^{-5}$ M/L | to $10^{-4}$ M/L |
| BSA | 0 | to 200 g/L | 50 g/L | to 150 g/L |
| CaCl$_2$ | 0 | to $2 \times 10^{-2}$ M/L | 0 | to $1 \times 10^{-2}$ M/L |
| Hydroxypropylcellulose | 0 | to 100 g/L | 25 g/L | to 75 g/L |
| Ropaque ™ OP-84 | 0 | to 10% | 0 | to 10% |
| Tris buffer | pH 7.0 | to pH 8.3 | pH 7.2 | to pH 7.8 |

In use, a blood sample having a volume of about 5 to 30 μl, typically obtained by a fingerstick device, is applied to the application face 16 of the porous membrane structure 12. After the sample has been applied, the test article 10 will be placed on an automated detector or test system 20 (FIG. 2) for reading the results of the coagulation assay. A test system 20 suitable for use with a fluorescent test article 10 includes a light source 22, a filter element 24, and a light detector 26. The light source 21 produces light 22 at a suitable excitation wavelength in order to induce fluorescence in the activated fluorescent reporter molecule of the substrate. Fluorescence results in emitted light 23 which passes through filter 24 which is selective for a suitable band fluorescence background and intensity between batches of reagents. The normalized value F'(t) is calculated as follows:

$$F'(t) = \frac{F(t) - F(20)}{F(240) - F(20)} \quad (1)$$

Next, the value t at which F'(t) first reaches 50% maximum is determined by linear interpolation between the F'(t) time points. This is designated as $T_{50}$. Finally, the prothrombin time, PT, is determined by a simple fit:

$$PT = lT_{50}^2 + nT_{50} + m \qquad (2)$$

where l, n, and m are determined experimentally.

If the reaction is performed on a constant temperature stage, no temperature correction is necessary. If the reaction is performed at ambient temperature, the temperature of the reagent is determined by a closely mounted thermocouple, and the PT time adjusted accordingly. A number of temperature adjustment algorithms are also possible. A relatively simple one is:

$$PT_{37} = PT_{ambient} - a(37 - temp_{ambient})PT_{ambient}^2 - b(37 - temp_{ambient})PT_{ambient} - C(37 - temp_{ambient}) \qquad (3)$$

where $T_{ambient}$ is the temperature of the reagent strip (measured in centigrade), $P_{37}$ is the temperature compensated prothrombin time (adjusted to a 37° C. reference temperature), and $PT_{ambient}$ is the PT result obtained from equation (2). The parameters a, b and c are determined experimentally. More sophisticated temperature corrections are also possible. Higher order polynomial fits can be used in both equation (2) and (3) as desired. Alternatively, the coefficients in equation (2) may be temperature compensated.

The following examples are offered by way of illustration, not by way of limitation.

EXPERIMENTAL

General Methodology

Fluorescence activity was monitored by observing the reacted membranes in a darkened chamber, illuminated with a 750 µW/cm² (at 15 cm) long wave (365 nm) ultraviolet lamp, held 30 cm from the sample. All reactions were conducted at room temperature (23° C.). Reaction kinetics were monitored by photographing the samples at defined intervals using a Minolta Maxxum 5000 SLR 35 mm camera equipped with a 50 mm lens. The photography used ASA 400 Kodak Gold color print film, exposed for 1- or 2-second exposures at f 5.6. To improve contrast, some photographs were shot using a Corion Corporation S40-450-R 450 nm filter (40 nm bandwidth). The filter allows the 460 nm fluorescence emission of the 7-amido-4-methylcoumarin fluorophores to pass, while reducing extraneous wavelengths. Timing was done manually with a stopwatch. Unless otherwise specified, all reagents were obtained from the Sigma Chemical Company, St. Louis, Mo. Instrumented observations were performed using a prototype instrument. The optics block used a Siemens BPW-34B photodetector mounted below a Corion Corporation S25-450-A 450 nanometer filter with a 25 nanometer bandwidth. An Edmund Scientific 10 mm×10 mm R32,601 prism cube beam splitter was mounted directly above the filter. The reagent was placed on top of the beam splitter, and illuminated from below using 365 nm wavelength UV light. The output from the photodetector was amplified by an instrumentation amplifier (described on page 89 of the *IC Users Casebook*, 1988, by Joseph Car, Howard Samms & Company), digitized by a 12 bit analog to digital converter, and recorded on an IBM-compatible personal computer. Temperature control (when done) was maintained using a Fisher model 147 isotemp dry bath.

Reagent-permeated membranes were prepared by adding sufficient liquid reagent mix to the membrane to totally saturate an exposed membrane section. Excess liquid reagent was then removed, and the saturated membrane air dried under a hot air blower at about 50° for 30 minutes. The dried membranes were stored in an air tight container, with silica gel desiccant, at room temperature until used.

Initial experiments focused on the coagulation neutrality test (criterion D discussed earlier). These studies used plasma only, and were tested using 15 µl samples of Sigma C-7916 level I coagulation control (activated partial thromboplastin time and prothrombin time within normal limits), Sigma C-8916 level II coagulation control (mildly elevated values for activated partial thromboplastin time and prothrombin time), or Sigma C 9916 Level III coagulation control (severely elevated levels for activated partial thromboplastin time and prothrombin time). Later experiments used whole blood in addition to the plasma controls. The whole blood samples were either non-anticoagulated fresh samples obtained from fingerstick samples, or citrate anticoagulated venous blood less than 8 hours old, and kept refrigerated until use. The thromboplastin used in these experiments was Sigma T-0263 rabbit brain thromboplastin at a concentration of 20 mg/ml. The bovine serum albumin (BSA) used was Sigma A-3294, protease-free fraction V powder. The thrombin substrate was N—t—Boc—Val—Pro—Arg-7-amido-4-methylcoumarin obtained from Sigma. The hydroxypropylcellulose used was Klucel®EF, obtained from Aqualon Corporation.

EXAMPLE 1

Effect of various membranes on the prothrombin time reaction

A liquid reagent mix was prepared by combining the following:
- 1200 µl 0.2M Tris buffer, pH 8.3
- 600 µl thromboplastin
- 100 µl 100 mM CaCl₂
- 100 mg BSA
- 100 µl of 1 mg/ml N—t—Boc—Val—Pro—Arg-7-amido-4-methylcoumarin Aliquots (100 µl) of the reagent mix were spotted onto five different membranes, as follows:
- Pall Corporation 1.2 micron Biodyne "B" (quarternary ammonia derivatized polyamide)
- Pall Corporation 1.2 micron Biodyne "C" (carboxy derivatized polyamide)
- Dominic Hunter 0.8 µm Asypor asymmetric cellulose membrane
- Whatman 3MM filter paper
- Schleicher & Schuell 593 filter paper
- Whatman GF/C glass fiber filter paper.

The coated membranes were tested with control I serum, allowed to react for 10 minutes, and visually assessed. The results were:

| Membrane | Reaction |
| --- | --- |
| Pall Corporation 1.2 micron Biodyne "B" | + (bright ring) |
| Pall Corporation 1.2 micron Biodyne "C" | − (no reaction) |
| Dominic Hunter Asypor | − |
| Whatman 3MM filter paper | − |
| Schleicher & Schuell 593 filter paper | − |
| Whatman GF/C glass fiber filter paper. | + (bright ring) |

The Whatman GF/C glass fiber filter paper acted as a positive control, since glass fiber materials are known to be compatible with certain coagulation pathways. The results showed that under these conditions, many membranes are not compatible with the extrinsic coagulation pathway. The results also showed that the fluorescence intensity on the reactive membranes was concentrated on a thin ring coinciding with the solvent front of the applied sample. This indicated that substantial chromatography of the thrombin substrate was occurring under these conditions. This is undesirable because a non-uniform distribution of fluorescence complicates interpretation of reaction kinetics.

EXAMPLE 2

Effect of various flow control agents

A liquid reagent mix was prepared by combining the following:

2000 µl 0.2M Tris buffer, pH 8.3
1 ml thromboplastin
150 µl 100 mM CaCl
150 mg BSA
150 µl 1 mg/ml N—t—Boc—Val—Pro—Arg-7-amido-4-methylcoumarin The mixture was divided into three, 1 ml aliquots. Nothing was added to the first aliquot. 50 mg of high molecular weight (Sigma D-5501 5,000,000–40,000,000 Mol. Wt.) dextran was added to the second aliquot, and 50 mg of Aqualon Klucel®EF (hydroxypropylcellulose) was added to the third aliquot. The three aliquots were mixed until fully dissolved and spotted onto 1.2 micron Pall Corporation Biodyne B membranes.

The coated membranes were tested with control I plasma and visually assessed. The results after ten minutes were:

| Flow Control Agent | Reaction |
| --- | --- |
| None | + (Bright ring) |
| Dextran | − (No reaction) |
| Klucel ® EF | + (Bright uniform circle) |

In the absence of a flow control agent, the fluorescent substrate continued to migrate with the sample solvent front as before. In contrast, the dextran addition inhibited the prothrombin time reaction. The Klucel®EF (hydroxypropylcellulose), however, thickened the reaction mixture enough to reduce chromatography without inhibiting the reaction. The result was a more uniform fluorescent signal. As a result of this experiment, Klucel®EF was added to the formulation on a routine basis. This experiment also illustrated the importance of using a coagulation neutral polymer.

EXAMPLE 3

Effect of calcium and thromboplastin on the prothrombin time reaction

One concern was that the apparent "prothrombin time" reaction that was observed in the previous experiments was actually some sort of non-physiological "artifact." To see if the observed reaction was, in fact, a genuine prothrombin time reaction, an experiment was done to see if the reaction required calcium and thromboplastin to proceed. Additionally, the ability of the reaction to distinguish between a normal control plasma, and an abnormal control plasma with a prolonged PT time, was tested. To do this, a number of different membrane cases with, and without, calcium and thromboplastin, were made up.

A liquid reagent mix was prepared by combining the following:

2 ml 0.2M Tris buffer, pH 8.3
150 mg BSA
150 mg Klucel®EF
150 µl of 1 mg/ml N—t—Boc—Val—Pro—Arg-7-amido-4-methylcoumarin The mixture was divided into two, 1 ml aliquots. 0.5 ml thromboplastin solution was added to one aliquot and 0.5 ml 0.2M Tris buffer, pH 8.3 was added to the other. These were the (+/−) thromboplastin cases.

Each case was further subdivided into two additional sub-cases. One of these had calcium, and one of these had EDTA (which binds calcium). This was done by dividing each case into two 0.5 ml samples. The (+) calcium case received 25 µl of 100 millimolar calcium chloride. The (−) calcium case received 25 µl of 100 mM Na$_2$EDTA. In all, four final cases resulted. These were:

(+) thromboplastin (+) CaCl$_2$
(+) thromboplastin (+) EDTA
(−) thromboplastin (+) CaCl$_2$
(−) thromboplastin (+) EDTA Samples of each solution were spotted onto Pall Corporation 1.2 micron Biodyne B, and dried. All four cases were then simultaneously challenged with control I and control II plasma, and observed. Intense fluorescence developed only in the (+) thromboplastin (+) CaCl$_2$ case with the control I (normal PT time) sample. All other cases were negative.

This experiment demonstrated that the observed reaction required both calcium and thromboplastin to work, and was capable of distinguishing a normal prothrombin time plasma from an abnormal prothrombin time plasma, providing good evidence that the system was performing a physiologically meaningful prothrombin time reaction.

EXAMPLE 4

Reagent kinetics with normal and abnormal prothrombin time serum

Other experiments (not shown) showed that the pH of the reagent mix had an effect on the relative sensitivity of the system towards samples with prolonged prothrombin times. In general, a pH closer to 7.5 tended to have greater sensitivity for detecting samples with prolonged prothrombin times. Thus the pH of the reaction cocktail was changed to 7.5 for subsequent experiments.

In the following experiment, the relative fluorescence intensity between control I and control II plasma was monitored by time lapse photography. A liquid reagent mix was prepared by combining the following:

1200 µl 0.2M Tris buffer, pH 7.5
600 µl tromoboplastin
100 µl 100 mM CaCl$_2$
100 mg BSA
100 mg Klucel®EF
100 µl of 1 mg/ml N—t—Boc—Val—Pro—Arg-7-amido-4-methylcoumarin The reagent was spotted onto Pall Corporation 1.2 micron Biodyne B as usual. The dried membranes were then challenged with control I and control II plasma, and photographed every minute. The results were:

| Time (min.) | Control I | Control II |
| --- | --- | --- |
| 0 | − | − |
| 1 | − | − |
| 2 | − | − |
| 3 | + | − |
| 4 | + | − |
| 5 | ++ | − |
| 6 | ++ | − |

-continued

| Time (min.) | Control I | Control II |
|---|---|---|
| 7 | ++ | − |
| 8 | ++ | + |
| 9 | ++ | ++ |

These results were again consistent with a physiologically meaningful prothrombin time reaction was occurring on the reagent membrane. As expected, the time of the appearance of the fluorescence signal in the abnormal (control II) sample was about twice that of the normal sample.

EXAMPLE 5

Effect of protein pre-treatment on prothrombin time reaction

The prothrombin time reactions obtained in previous experiments were unacceptably long. It was hypothesized that the long reaction times might have been due to inactivation of labile coagulation factors upon the membrane. It was further hypothesized that this inactivation might be blocked by adding an excess of a coagulation compatible protein to the system. To test this hypothesis, a "blocking solution" containing of 0.05M Tris pH 7.5 and 2% protease-free bovine serum albumin (BSA) was made up, and membrane samples were either treated with this solution for 12 hours at room temperature followed by air drying, or were tested untreated.

The following membranes were pre-treated:
Pall Corporation 1.2 micron Biodyne "B"
Gelman Supor 800
Filterite/Memtec 0.45 micron asymmetric polysulfone
Dominic Hunter 0.8 micron Asypor
Schleicher & Schuell 34 G glass fiber filter paper.

In this experiment, and all following experiments, the BSA component of the reaction cocktail was doubled over the previous cases, based upon the observations that BSA was having a protective effect on the coagulation factors.

A liquid reagent mix was prepared by combining the following:
1200 μl Tris buffer, pH 7.5
600 μl thromboplastin
200 μl 100 mM CaCl$_2$
200 mg protease free BSA
100 mg Klucel®EF
100 μl 1 mg/ml N—t—Boc—Val—Pro—Arg-7-amido-4-methylcoumarin Samples of these membranes, and the corresponding untreated membranes, were affixed to a test stand, and saturated with the reagent mixture, and air dried as usual.

The samples were then exposed to level I and II coagulation controls, and tested. Reaction times were dramatically decreased. The effect of pre-treatment was most pronounced for the level II, (prolonged PT time) control. The level I controls (not shown) were correspondingly faster (typically 2 minutes for all samples in this series), and were not noticeably affected by the presence or absence of pre-treatment.

Note that for all samples, omitting thromboplastin from the reaction mixture prevented any signal from occurring. Results (level II control):

|  | 1 min | 2 min | 3 min | 4 min | 5 min | 6 min |
|---|---|---|---|---|---|---|
| Untreated: |  |  |  |  |  |  |
| Biodyne | − | − | − | − | − | − |
| Supor | − | − | − | − | − | − |
| Asymmetric | − | − | + | + | + | + |
| Asypor | − | − | − | − | − | − |
| 34 G | − | − | + | + | + | + |
| Treated: |  |  |  |  |  |  |
| Biodyne | − | − | − | + | + | + |
| Supor | − | − | − | − | − | − |
| Asymmetric | − | − | + | + | + | + |
| Asypor | − | − | − | − | − | − |
| 34 G | − | − | + | + | + | + |

Note that in the absence of pre-treatment, Biodyne B was essentially unreactive to level II control for up to 6 minutes. By contrast, pre-treatment increased the sensitivity of Biodyne B to level II control, so that a detectable reaction now occured by 4 minutes.

Asymmetric polysulfone exhibited superior coagulation neutrality, however. This is shown by a faster level II PT reaction, indicating that less inactivation of coagulation factors had occurred on this membrane substrate. The coagulation neutrality of this membrane, already good before pre-treatment, was not measurably changed after pre-treatment.

The membranes were also challenged with a sample of whole blood, with had a normal prothrombin time. The results were:

|  | 1 min | 2 min | 3 min | 4 min | 5 min | 6 min |
|---|---|---|---|---|---|---|
| Membrane (Untreated): |  |  |  |  |  |  |
| Biodyne | − | − | − | − | − | − |
| Supor | − | − | − | − | − | − |
| Asymmetric | − | − | − | + | + | + |
| Asypor | − | − | − | − | − | − |
| 34 G | − | − | − | − | − | − |
| Membrane (Treated): |  |  |  |  |  |  |
| Biodyne | − | − | − | − | − | − |
| Supor | − | − | − | − | − | − |
| Asymmetric | − | − | + | + | + | + |
| Asypor | − | − | − | − | − | − |
| 34 G | − | − | − | − | − | − |

The results show that although Biodyne "B" and Supor-800 membranes gave a good signal with normal, Level I, coagulation control plasma, they gave no fluorescent signal at all with whole blood. By contrast, asymmetric polysulfone continued to give a signal. At a longer (10 minute) time point, Schleicher & Schuell 34 G, a glass fiber material which filters red cells from plasma, also gave a positive signal with whole blood. Thus of the materials tested, asymmetric polysulfone was the best for whole blood assays.

EXAMPLE 6

Effect of hydroxypropylcellulose (a flow control reagent) on the prothrombin time reaction on asymmetric polysulfone The effect of hydroxypropylcellulose on asymmetric polysulfone was tested.

A liquid reagent mix was prepared by combining the following:
1200 μl Tris buffer, pH 7.5
600 μl thromboplastin
200 μl CaCl$_2$ 200 mg BSA The mixture was divided into two, 1 ml aliquots. 50 mg of Klucel®EF was added to one, and nothing was added to the other. After the Klucel®EF had dissolved, 50 µl of 1 mg/ml N—t—Boc—Val—Pro—Arg-7-amido-4-methylcoumarin was added to both samples.

Each case was applied to a sample of 0.45 micron asymmetric polysulfone membrane on the open pore side. Excess sample was removed, and the membranes air dried as usual.

All four cases were then simultaneously challenged with control I, control II and control III plasma. The cases were then observed as usual. Results:

|  |  | 1 min | 2 min | 3 min | 4 min | 5 min | 6 min |
|---|---|---|---|---|---|---|---|
| (−) | Klucel ® EF | | | | | | |
| | Control I | − | ring+ | + | + | + | + |
| | Control II | − | − | ring+ | + | + | + |
| | Control III | − | − | − | − | ring+ | ring+ |
| (+) | Klucel ® EF | | | | | | |
| | Control I | − | + | + | + | + | + |
| | Control II | − | − | + | + | + | + |
| | Control III | − | − | − | − | + | + |

Although the kinetics and the fluorescence intensity of the two cases were very similar, the (−) Klucel-®EF cases had a tendency to first develop color in a ring at the solvent front, and later to develop a uniform color throughout the sample. By contrast, the (+) Klucel®EF cases developed a uniform color from the beginning without the tendency to form a ring. Thus Klucel®EF was maintained in the formulation to reduce chromatography effects.

EXAMPLE 7

Prothrombin time "test-strip"

This experiment demonstrated that a single layer composition could be produced that could distinguish normal (Level I) control from mildly abnormal (Level II) control, from severely abnormal (Level III) control, and that this single layer composition could also function using a small drop of whole blood. The experiment further demonstrated that this reaction would require thromboplastin to function.

This experiment again used the 0.45 micron pore size asymmetric polysulfone membrane obtained from Filterite/Memtec Corporation. To enhance biocompatibility, the membrane had been pre-treated by exposure to a solution of 2% protease free bovine serum albumin in 0.05M Tris buffer at pH 7.5 for 12 hours, followed by air drying.

Although the asymmetric membranes were giving a positive fluorescent signal with whole blood, the intensity of the signal was still less than that of serum alone. To see if pigments could enhance the whole blood signal further, this experiment also investigated the effect of doping the membrane with Ropaque®, which is a pigment composed of small, hollow, 0.5 micron sized particles of a styrene/acrylic polymer produced by the Rohm & Haas corporation.

A liquid reagent mix was prepared by combining the following:

800 µl of 0.2M Tris buffer, pH 7.5
200 µl of 100 mM CaCl$_2$
200 mg of BSA
100 mg Klucel®EF
100 µl of 1 mg/ml N—t—Boc—Val—Pro—Arg-7-amido-4-methylcoumarin The mixture was divided into two, 550 µl aliquots. 300 µl of thromboplastin was added to one, 300 µl of H$_2$O was added to the other. These were the +/− thromboplastin cases. Each aliquot was in turn divided into two, 400 µl aliquots. One aliquot received 100 µl of a 50% Ropaque® suspension, and the other aliquot received 100 µl of H$_2$O. These were the (+/−) Ropaque® cases. In all, four final cases resulted. These were:

(+) thromboplastin (+) Ropaque®
(+) thromboplastin (−) Ropaque®
(−) thromboplastin (+) Ropaque®
(−) thromboplastin (−) Ropaque®

Each case was applied to a sample of 0.45 micron asymmetric polysulfone membrane on the open pore side. Excess sample was removed, and the membranes air dried as usual.

All four cases were then simultaneously challenged with control I, control II and control III plasma, as well as a sample of normal whole blood. The cases were then observed as usual. Fluorescence developed in the (+) thromboplastin cases according to the following table:

|  |  | 1 min | 2 min | 3 min | 4 min | 5 min | 6 min |
|---|---|---|---|---|---|---|---|
| (+) thromboplastin case: | | | | | | | |
| (−) | Ropaque ® | | | | | | |
| | Control I | − | + | + | + | + | + |
| | Control II | − | − | + | + | + | + |
| | Control III | − | − | − | − | + | + |
| | blood | − | − | ring+ | ring+ | ring+ | ring+ |
| (+) | Ropaque ® | | | | | | |
| | Control I | − | + | + | + | + | + |
| | Control II | − | − | + | + | + | + |
| | Control III | − | − | − | − | + | + |
| | blood | − | − | + | + | + | + |
| (−) thromboplastin case: | | | | | | | |
| (−) | Ropaque ® | | | | | | |
| | Control I | − | − | − | − | − | − |
| | Control II | − | − | − | − | − | − |

|  |  | 1 min | 2 min | 3 min | 4 min | 5 min | 6 min |
|---|---|---|---|---|---|---|---|
|  | Control III | − | − | − | − | − | − |
|  | blood | − | − | − | − | − | − |
| (+) | Ropaque ® |  |  |  |  |  |  |
|  | Control I | − | − | − | − | − | − |
|  | Control II | − | − | − | − | − | − |
|  | Control III | − | − | − | − | − | − |
|  | blood | − | − | − | − | − | − |

No fluorescence developed in any of the (−) Thromboplastin cases, indicating that thromboplastin is required for this reaction.

The (+) Ropaque ® cases generally gave a stronger fluorescent signal than the (−) Ropaque ® cases, and additionally had a tendency to give a more uniform fluorescent distribution. Thus Ropaque ® appeared to be beneficial.

Each case was applied to a sample of 0.45 micron asymmetric polysulfone membrane on the open pore side. Excess sample was removed, and the membranes air dried as usual.

All four cases were then simultaneously challenged with control I, control II and control III plasma, as well as a sample of normal whole blood. The cases were then observed as usual.

|  |  | 1 min | 2 min | 3 min | 4 min | 5 min | 6 min |
|---|---|---|---|---|---|---|---|
| (+) $CaCl_2$ CASE: |  |  |  |  |  |  |  |
| (−) | Ropaque ® |  |  |  |  |  |  |
|  | Control I | − | + | + | + | + | + |
|  | Control II | − | − | + | + | + | + |
|  | Control III | − | − | − | − | + | + |
|  | blood | − | − | + | + | + | ring+ |
| (+) | Ropaque ® |  |  |  |  |  |  |
|  | Control I | − | + | + | + | + | + |
|  | Control II | − | − | + | + | + | + |
|  | Control III | − | − | − | − | + | + |
|  | blood | − | − | + | + | + | + |
| (−) $CaCl_2$ CASE: |  |  |  |  |  |  |  |
| (−) | Ropaque ® |  |  |  |  |  |  |
|  | Control I | − | − | − | − | − | − |
|  | Control II | − | − | − | − | − | − |
|  | Control III | − | − | − | − | − | − |
|  | blood | − | − | + | + | + | ring+ |
| (+) | Ropaque ® |  |  |  |  |  |  |
|  | Control I | − | − | − | − | − | − |
|  | Control II | − | − | − | − | − | − |
|  | Control III | − | − | − | − | − | − |
|  | blood | − | − | + | + | + | + |

EXAMPLE 8

Effect of calcium

A parallel experiment to the previous experiment was done to study the effect of calcium on the prothrombin time reaction, and to confirm that the Ropaque ® consistently enhanced the fluorescence signal with whole blood.

A liquid reagent mix was prepared by combining the following:

800 µl 0.2M Tris pH 7.5
600 µl thromboplastin
200 mg BSA
100 mg Klucel ® EF
100 mg 1 mg/ml N—t—Boc—Val—Pro—Arg-7-amido-4-methylcoumarin Divided into two 0.75 milliliter aliquots. Added 100 µl of 100 mM $CaCl_2$ to one, 100 µl of $H_2O$ to the other. Each aliquot was further subdivided into two, 0.4 milliliter aliquots. 100 µl of a 50% Ropaque ® suspension was added to one, and 100 µl of $H_2O$ was added to the other. In all, four cases resulted. These were:

(+) $CaCl_2$ (+) Ropaque ®
(+) $CaCl_2$ (−) Ropaque ®
(−) $CaCl_2$ (+) Ropaque ®
(−) $CaCl_2$ (−) Ropaque ®

Note an important difference between the (−) $CaCl_2$ case in this experiment, and the (−) thromboplastin case in the previous experiment. Although no reaction was obtained with whole blood in the (−) thromboplastin case, a normal reaction was obtained with whole blood in the (−) $CaCl_2$ case. This was because the fresh whole blood used here contained sufficient calcium to trigger the extrinsic pathway without the necessity for adding extra calcium to the reagent. By contrast, the plasma controls, which had their calcium levels depleted by use of a calcium chelator, were unreactive in the (−) $CaCl_2$ case.

This was a useful finding, in view of prior art showing that superior reagent stability can be achieved if calcium is not stored with thromboplastin. Since a home test needs good reagent stability, and will function exclusively with whole blood, superior results may be obtained if the formulation does not contain calcium.

Ropaque ® continued to have a beneficial effect, with whole blood, by enhancing the intensity of the fluorescent signal, somewhat, and by increasing the uniformity of the signal. However, it should be noted that adequate results were also obtained without Ropaque ®.

EXAMPLE 9

Variable sample size studies

A good home test will be tolerant in variations in the amount of whole blood added to the reagent, and will preferably work using extremely small sample sizes, down to about 5 µl. In this experiment, samples of the (−) CaCl$_2$(−) Ropaque® and the (+) CaCl$_2$ (+) Ropaque® material left over from experiment 8 were challenged with 5, 10 and 20 µl of whole blood. For both cases, the reaction kinetics and the intensity of the fluorescence reaction were identical for all sample sizes. By contrast, when the identical experiment was performed with Schleicher & Schuell 34G or Whatman GF/C glass fiber filter papers, no reaction at all was seen with the 5 µl and 10 µl whole blood samples.

EXAMPLE 10

Quantitative studies with whole blood samples

The purpose of this experiment was to obtain quantitative data on the performance of the reagent in order to facilitate optimization of the system.

A liquid reagent mix was prepared by combining the following:
- 2400 µl Tris pH 7.5
- 1200 µl Thromboplastin
- 400 µl 100 mM CaCl$_2$
- 400 mg BSA
- 200 mg Klucel®EF
- 200 µl of 1 mg/ml N—t—Boc—Val—Pro—Arg-7-amido-4-methylcoumarin This was applied to a sample of 0.45 micron asymmetric polysulfone membrane on the open pore side. Excess sample was removed, and the membrane air dried as usual.

The membrane was processed into individual reagent strips. This was done by placing a strip of ⅜" wide 3M Scotch ™ Cat. 136 double stick tape onto a 10 mil thick rigid opaque support, and punching ¼" diameter holes through the center of the tape and through the support. Treated membrane was then laminated to the tape, narrow pore size down. The reagent strips where then cut to a convenient size, and mounted above the viewing area of the instrument described previously.

Blood samples were obtained as described previously. These samples were applied to the reagent strips, and were observed at 10 second intervals for a total of 4 minutes (240 seconds). The experiment was conducted at room temperature (25° C.).

Figure 3:
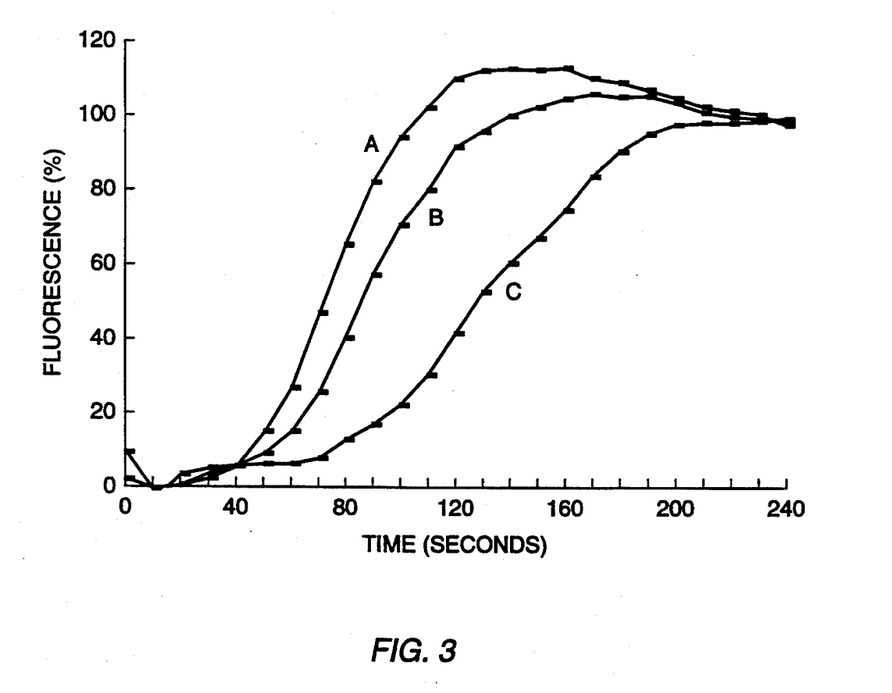
FIG. 3 is the result from an experiment using the test article shown in FIG. 1 and the test system shown in FIG. 2. In this experiment, a whole blood sample with a normal prothrombin time was compared to a whole blood sample with a slightly prolonged prothrombin time and a whole blood sample with a severely prolonged prothrombin time.

The results obtained for a normal blood sample (A), a blood sample with a slightly prolonged prothrombin time (B), and a blood sample with a severely prolonged prothrombin time (C) are shown in FIG. 3.

The results show that the system is able to clearly distinguish among the various whole blood samples.

Although the foregoing invention has been described in some detail by way of illustration and example, for purposes of clarity of understanding, it will be obvious that certain changes and modifications may be practiced within the scope of the appended claims.

What is claimed is:

1. A test article comprising:
   a single permeable membrane having an application face and an opposite indicator face, said membrane being substantially free from interference with a coagulation pathway, being non-lytic to red blood cells, and having a pore site and distribution which excludes penetration of red blood cells from the application face to the indicator face;
   a coagulation initiator impregnated within the membrane; and
   a substrate impregnated within the membrane, which substrate produces a detectable fluorescent signal upon activation by a coagulation pathway proteolytic enzyme;
   wherein the test article is dry and whereby whole blood may be applied to the application face of the membrane and a detectable fluorescent signal is produced on the indicator face as a result of production of the coagulation pathway proteolytic enzyme.

2. A test article as in claim 1, wherein the permeable membrane is composed of a hydrophilic, non-swellable material which is free from interference with the coagulation pathway.

3. A test article as in claim 2, wherein the material is polysulfone.

4. A test article as in claim 3, wherein the polysulfone has an asymmetric structure.

5. A test article as in claim 1, wherein the permeable membrane is hydrophilic, non-swellable material which has been blocked with a protein to inhibit interference with the coagulation pathway.

6. A test article as in claim 1, wherein the coagulation initiator initiates the extrinsic coagulation pathway.

7. A test article as in claim 6, wherein the coagulation initiator is thromboplastin.

8. A test article as in claim 1, wherein the coagulation initiator initiates the intrinsic coagulation pathway.

9. A test article as in claim 8, wherein the coagulation initiator is selected from the group consisting of ellagic acid, kaolin, and silica.

10. A test article as in claim 1, wherein the coagulation pathway proteolytic enzyme which activates the substrate is thrombin.

11. A test article as in claim 10, wherein the substrate is a peptide cleavably attached to a reporter molecule, where thrombin binds the peptide and cleaves the reporter molecule from the peptide to produce the detectable fluorescent signal.

12. A test article as in claim 1, further comprising a buffer impregnated within the membrane which maintains a pH compatible with the coagulation pathway and the membrane.

13. A test article as in claim 1, further comprising calcium cation impregnated within the membrane.

14. A test article as in claim 1, further comprising light scattering pigment particles impregnated within the membrane.

15. A test article as in claim 1, further comprising a flow control agent impregnated within the membrane, which flow control agent is a high molecular weight polymer which increases the viscosity of fluids applied to the membrane.

16. A test article comprising:
   a permeable asymmetric polysulfone membrane having opposite faces;
   thromboplastin impregnated within the membrane; and
   a thrombin substrate impregnated within the membrane, said substrate comprising a thrombin-binding peptide cleavably attached to a fluorescent reporter molecule whereby thrombin releases the fluorescent reporter from the substrate;

whereby whole blood may be applied to one face of the membrane and fluorescence detected on an opposite face as a result of thrombin-mediated cleavage of the thrombin substrate.

17. A test article as in claim 16, further comprising a buffer impregnated within the membrane which maintains a pH compatible with a coagulation pathway and the membrane.

18. A test article as in claim 16, further comprising calcium cation impregnated within the membrane.

19. A test article as in claim 16, further comprising light scattering pigment particles impregnated within the membrane.

20. A test article as in claim 16, further comprising a flow control agent impregnated within the membrane, which flow control agent increases the viscosity of fluids applied to the membrane.

21. A method for determining coagulation capability of a patient, said method comprising:

applying a whole blood sample to an application face of a permeable membrane, wherein the membrane is substantially free from interference with a coagulation pathway, is non-lytic to red blood cells, and has a pore size and distribution which excludes penetration of red blood cells from the application face to an opposite indicator face, and wherein a coagulation initiator and a substrate which produces a detectable fluorescent signal upon activation by a coagulation pathway proteolytic enzyme are both impregnated within the membrane; and detecting the fluorescent signal at the indicator face of the membrane, wherein the fluorescent signal results from production of the coagulation pathway proteolytic enzyme within the membrane which had been initiated by interaction of the coagulation initiator with the blood sample.

22. A method as in claim 21, wherein the blood sample is not measured prior to applying the sample to the membrane.

23. A method as in claim 22, wherein the blood sample is obtained by a finger prick.

24. A method as in claim 21, performed at room temperature.

25. A method as in claim 21, performed at a controlled temperature.

26. A method as in claim 21, wherein the detectable signal is temperature compensated.

27. A method as in claim 21, wherein the substrate produces a fluorescent signal upon activation by thrombin present in the whole blood sample.

* * * * *